United States Patent
Collins et al.

(10) Patent No.: US 7,722,579 B2
(45) Date of Patent: *May 25, 2010

(54) DEVICES FOR INJECTING A CURABLE BIOMATERIAL INTO A INTERVERTEBRAL SPACE

(75) Inventors: Keith Collins, Milford, CT (US); Lawrence Boyd, Durham, CT (US); Andrew Carter, Trumbull, CT (US); Dennis Lee, Milford, CT (US); John Pafford, Eads, TN (US); Jared Walkenhorst, Fairfield, CT (US); Thomas G. Wilson, Guilford, CT (US); Mark D. LoGuidice, Southport, CT (US); Lance Middlelton, Soddy Daisy, TN (US)

(73) Assignee: Spine Wave, Inc., Shelton, CT (US)

( * ) Notice: Subject to any disclaimer, the term of this patent is extended or adjusted under 35 U.S.C. 154(b) by 18 days.

This patent is subject to a terminal disclaimer.

(21) Appl. No.: 11/170,010

(22) Filed: Jun. 29, 2005

(65) Prior Publication Data
US 2006/0009779 A1 Jan. 12, 2006

Related U.S. Application Data

(60) Provisional application No. 60/583,665, filed on Jun. 29, 2004.

(51) Int. Cl.
*A61M 25/00* (2006.01)
(52) U.S. Cl. .......................... 604/264; 604/57; 604/122; 604/174; 604/272
(58) Field of Classification Search .................. 604/57, 604/164.03, 164.11, 167.01–167.04, 167.06, 604/174, 175, 239, 264, 272; 606/92–95
See application file for complete search history.

(56) References Cited

U.S. PATENT DOCUMENTS

| 3,750,667 A | 8/1973 | Pshenichny et al. |
| 3,893,445 A | 7/1975 | Hofsess |

(Continued)

FOREIGN PATENT DOCUMENTS

| EP | 0 277 282 | 8/1991 |
| FR | 2 639 823 | 12/1988 |
| WO | 9100713 A1 | 1/1991 |
| WO | 0168005 A2 | 9/2001 |

OTHER PUBLICATIONS

Premarket Notification [510(k)] Summary, "Kyphx Directional Inflatable Bone Tamps", Kyphx Directional Inflatable Bone Tamp-Traditional 510(k), Kyphon Inc., Sep. 15, 2003, 5 pages).
510(k) Summary of Safety and Effectiveness, "KyphX™ Inflatable Bone Tamp", Feb. 14, 2001, 5 pages.

(Continued)

*Primary Examiner*—Kevin C Sirmons
*Assistant Examiner*—Bhisma Mehta
(74) *Attorney, Agent, or Firm*—Maginot, Moore & Beck LLP

(57) ABSTRACT

A vented needle assembly is provided for sealably injecting biomaterial into an intradiscal space interiorly of the annulus of a spinal disc and for providing an exhaust for the intradiscal space. The vented needle assembly comprises a compressible seal body for pressing against an outer surface of the annulus, and a needle extending through the seal. The needle may be configured to connect to a syringe for pressure injection of the biomaterial. The seal includes a vent extending therethrough with an opening for communication with the intradiscal space and an opening for the discharge of excess biomaterial filling the intradiscal space. A kit of parts is also provided for use in the treatment of a spinal disc, the kit comprising the vented needle assembly and an inflatable trial device. The trial device is removably introduced into the intradiscal space and inflated to determine the available size of the intradiscal space.

18 Claims, 9 Drawing Sheets

U.S. PATENT DOCUMENTS

| | | | |
|---|---|---|---|
| 4,132,746 A | 1/1979 | Urry et al. |
| 4,142,517 A | 3/1979 | Stavropoulos et al. |
| 4,187,852 A | 2/1980 | Urry et al. |
| 4,313,434 A | 2/1982 | Segal |
| 4,474,851 A | 10/1984 | Urry |
| 4,492,576 A | 1/1985 | Dragan |
| 4,500,700 A | 2/1985 | Urry |
| 4,545,374 A | 10/1985 | Jacobson |
| 4,589,882 A | 5/1986 | Urry |
| 4,609,551 A | 9/1986 | Caplan et al. |
| 4,684,363 A | 8/1987 | Ari et al. |
| 4,736,738 A | 4/1988 | Lipovsek et al. |
| 4,772,287 A | 9/1988 | Ray et al. |
| 4,783,523 A | 11/1988 | Urry et al. |
| 4,793,351 A | 12/1988 | Landman et al. |
| 4,870,055 A | 9/1989 | Urry et al. |
| 4,898,962 A | 2/1990 | Chan et al. |
| 4,904,260 A | 2/1990 | Ray et al. |
| 4,911,718 A | 3/1990 | Lee et al. |
| 4,938,763 A | 7/1990 | Dunn et al. |
| 4,969,888 A | 11/1990 | Scholten et al. |
| 5,064,430 A | 11/1991 | Urry |
| 5,108,404 A | 4/1992 | Scholten et al. |
| 5,156,606 A * | 10/1992 | Chin ..................... 606/86 |
| 5,219,328 A | 6/1993 | Morse et al. |
| 5,235,041 A | 8/1993 | Cappello et al. |
| 5,258,043 A | 11/1993 | Stone |
| 5,259,971 A | 11/1993 | Smith Morse et al. |
| 5,300,035 A | 4/1994 | Clement |
| 5,318,524 A | 6/1994 | Morse et al. |
| 5,331,975 A | 7/1994 | Bonutti |
| 5,344,439 A | 9/1994 | Otten |
| 5,411,491 A * | 5/1995 | Goldhardt et al. ........... 604/247 |
| 5,431,676 A | 7/1995 | Dubrul et al. |
| 5,443,514 A | 8/1995 | Steffee |
| 5,454,365 A | 10/1995 | Bonutti |
| 5,505,732 A | 4/1996 | Michelson |
| 5,514,153 A | 5/1996 | Bonutti |
| 5,549,565 A | 8/1996 | Ryan et al. |
| 5,556,429 A | 9/1996 | Felt |
| 5,562,736 A | 10/1996 | Ray et al. |
| 5,641,648 A | 6/1997 | Ferrari et al. |
| 5,645,597 A | 7/1997 | Krapiva |
| 5,667,520 A | 9/1997 | Bonutti |
| 5,681,289 A | 10/1997 | Wilcox et al. |
| 5,685,826 A | 11/1997 | Bonutti |
| 5,697,889 A | 12/1997 | Slotman et al. |
| 5,702,446 A | 12/1997 | Schenck et al. |
| 5,716,416 A | 2/1998 | Lin |
| 5,720,726 A | 2/1998 | Marcadis et al. |
| 5,722,977 A | 3/1998 | Wilhelmy |
| 5,723,588 A | 3/1998 | Donofrio et al. |
| 5,752,969 A | 5/1998 | Cunci et al. |
| 5,760,004 A | 6/1998 | Stedronsky |
| 5,762,629 A | 6/1998 | Kambin |
| 5,770,697 A | 6/1998 | Ferrari et al. |
| 5,773,249 A | 6/1998 | Cappello et al. |
| 5,773,577 A | 6/1998 | Cappello |
| 5,800,549 A | 9/1998 | Bao et al. |
| 5,808,012 A | 9/1998 | Donofrio et al. |
| 5,817,303 A | 10/1998 | Stedronsky et al. |
| 5,827,318 A | 10/1998 | Bonutti |
| 5,830,713 A | 11/1998 | Ferrari et al. |
| 5,860,997 A | 1/1999 | Bonutti |
| 5,874,500 A | 2/1999 | Rhee et al. |
| 5,885,251 A * | 3/1999 | Luther ..................... 604/161 |
| 5,888,220 A | 3/1999 | Felt et al. |
| 5,936,035 A | 8/1999 | Rhee et al. |
| 5,954,739 A | 9/1999 | Bonutti |
| 5,962,648 A | 10/1999 | Berg |
| 5,968,062 A | 10/1999 | Thomas et al. |
| 6,004,782 A | 12/1999 | Daniell et al. |
| 6,015,474 A | 1/2000 | Stedronsky |
| 6,017,305 A | 1/2000 | Bonutti |
| 6,017,350 A | 1/2000 | Long |
| 6,018,030 A | 1/2000 | Ferrari et al. |
| 6,018,094 A | 1/2000 | Fox |
| 6,030,401 A | 2/2000 | Marino |
| 6,033,654 A | 3/2000 | Stedronsky et al. |
| 6,039,761 A | 3/2000 | Li et al. |
| 6,042,596 A | 3/2000 | Bonutti |
| 6,048,346 A | 4/2000 | Reiley et al. |
| 6,051,648 A | 4/2000 | Rhee et al. |
| 6,063,378 A | 5/2000 | Nohara et al. |
| 6,083,202 A | 7/2000 | Smith |
| 6,086,595 A | 7/2000 | Yonemura et al. |
| 6,110,484 A | 8/2000 | Sierra |
| 6,111,165 A | 8/2000 | Berg |
| 6,113,639 A | 9/2000 | Ray et al. |
| 6,123,687 A | 9/2000 | Simonyi et al. |
| 6,126,682 A | 10/2000 | Sharkey et al. |
| 6,135,999 A | 10/2000 | Fanton et al. |
| 6,140,072 A | 10/2000 | Ferrari et al. |
| 6,140,452 A | 10/2000 | Felt et al. |
| 6,165,489 A | 12/2000 | Berg et al. |
| 6,166,130 A | 12/2000 | Rhee et al. |
| 6,174,311 B1 | 1/2001 | Branch et al. |
| 6,183,518 B1 | 2/2001 | Ross et al. |
| 6,184,348 B1 | 2/2001 | Ferrari et al. |
| 6,187,023 B1 | 2/2001 | Bonutti |
| 6,187,048 B1 | 2/2001 | Milner et al. |
| 6,206,921 B1 | 3/2001 | Guagliano et al. |
| 6,210,397 B1 | 4/2001 | Aboul-Hosn et al. |
| 6,224,599 B1 | 5/2001 | Baynham et al. |
| 6,224,607 B1 | 5/2001 | Michelson |
| 6,224,630 B1 | 5/2001 | Bao et al. |
| 6,245,107 B1 | 6/2001 | Ferree |
| 6,248,110 B1 | 6/2001 | Reiley et al. |
| 6,248,131 B1 | 6/2001 | Felt et al. |
| 6,258,872 B1 | 7/2001 | Stedronsky |
| 6,261,311 B1 | 7/2001 | Sharkey et al. |
| 6,264,659 B1 | 7/2001 | Ross et al. |
| 6,277,122 B1 | 8/2001 | McGahan et al. |
| 6,277,394 B1 | 8/2001 | Sierra |
| 6,306,177 B1 | 10/2001 | Felt et al. |
| 6,312,469 B1 | 11/2001 | Gielen et al. |
| 6,312,725 B1 | 11/2001 | Wallace et al. |
| 6,323,278 B2 | 11/2001 | Rhee et al. |
| 6,332,894 B1 | 12/2001 | Stalcup et al. |
| 6,340,369 B1 | 1/2002 | Ferree |
| 6,344,058 B1 | 2/2002 | Ferree |
| 6,344,488 B1 | 2/2002 | Chenite et al. |
| 6,355,776 B1 | 3/2002 | Ferrari et al. |
| 6,370,420 B1 | 4/2002 | Kraft |
| 6,371,990 B1 | 4/2002 | Ferree |
| 6,380,154 B1 | 4/2002 | Cappello et al. |
| 6,395,007 B1 | 5/2002 | Bhatnagar et al. |
| 6,402,750 B1 | 6/2002 | Atkinson et al. |
| 6,402,784 B1 | 6/2002 | Wardlaw |
| 6,413,742 B1 | 7/2002 | Olsen et al. |
| 6,423,333 B1 | 7/2002 | Stedronsky et al. |
| 6,425,919 B1 | 7/2002 | Lambrecht |
| 6,428,576 B1 | 8/2002 | Haldimann |
| 6,428,978 B1 | 8/2002 | Olsen et al. |
| 6,436,143 B1 | 8/2002 | Ross et al. |
| 6,440,138 B1 | 8/2002 | Reiley et al. |
| 6,443,988 B2 | 9/2002 | Felt et al. |
| 6,447,512 B1 | 9/2002 | Landry et al. |
| 6,482,235 B1 | 11/2002 | Lambrecht et al. |
| 6,500,205 B1 | 12/2002 | Michelson |
| 6,508,839 B1 | 1/2003 | Lambrecht et al. |
| 6,558,390 B2 | 5/2003 | Cragg |
| 6,579,291 B1 | 6/2003 | Keith et al. |
| 6,592,625 B2 | 7/2003 | Cauthen |

| | | |
|---|---|---|
| 6,595,998 B2 | 7/2003 | Johnson et al. |
| 6,726,691 B2 | 4/2004 | Osorio et al. |
| 6,805,695 B2 | 10/2004 | Keith et al. |
| 6,814,736 B2 | 11/2004 | Reiley et al. |
| 6,981,981 B2 | 1/2006 | Reiley et al. |
| 7,004,945 B2 * | 2/2006 | Boyd et al. .................. 606/92 |
| 2001/0021852 A1 | 9/2001 | Chappius |
| 2002/0032155 A1 | 3/2002 | Ferree |
| 2002/0045942 A1 | 4/2002 | Ham |
| 2002/0049527 A1 | 4/2002 | Kohno et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147497 A1 | 10/2002 | Belef et al. |
| 2002/0151980 A1 | 10/2002 | Cauthen |
| 2002/0156531 A1 | 10/2002 | Felt et al. |
| 2002/0189622 A1 | 12/2002 | Cauthen, III et al. |
| 2003/0009227 A1 | 1/2003 | Lambrecht et al. |
| 2003/0033017 A1 | 2/2003 | Lotz et al. |
| 2003/0082169 A1 | 5/2003 | Boyd |
| 2003/0083641 A1 | 5/2003 | Angel et al. |
| 2003/0083642 A1 * | 5/2003 | Boyd et al. ................ 604/506 |
| 2003/0120345 A1 | 6/2003 | Cauthen |
| 2004/0059339 A1 | 3/2004 | Roehm, III et al. |
| 2004/0068268 A1 * | 4/2004 | Boyd et al. .................. 606/92 |
| 2004/0073213 A1 | 4/2004 | Serhan et al. |
| 2004/0098017 A1 | 5/2004 | Saab et al. |
| 2004/0186471 A1 | 9/2004 | Trieu |
| 2004/0229878 A1 | 11/2004 | DiMauro et al. |
| 2005/0070913 A1 | 3/2005 | Milbocker et al. |
| 2005/0102030 A1 | 5/2005 | Yuksel et al. |
| 2005/0209555 A1 | 9/2005 | Middleton et al. |
| 2005/0209601 A1 | 9/2005 | Bowman et al. |
| 2005/0209602 A1 | 9/2005 | Bowman et al. |
| 2005/0234425 A1 | 10/2005 | Miller et al. |

OTHER PUBLICATIONS

Boyd, Lawrence M., Mahar, Andrew and Cappello, Joseph, "Injectable Biomaterials for Augmentation of the Nucleus Pulposus", International Symposium-Non-Fusion Techniques in Spinal Surgery, Feb. 14, 2003, 12pages.

Mahar et al., "Biomechanical Efficacy of a Protein Polymer Hydrogel for Inter-Vertebral Nucleus Augmentation and Replacement", World Congress of Biomechanics, Calgay, Canada, Aug. 5, 2002, 4 pages.

Kitchel, Scott and Cappello, Joseph, "Injectable Biomaterials for Augmentation of the Nucleus Pulposus", http://127.0.0.1:8080/SAS3C1/presentation_list8.php, Apr. 25, 2005, 6 pages.

Garfin, Steven R. Yuan, Hansen A., and Reiley, Mark A., "Kyphoplasty and Vertebroplasty for the Treatment of Painful Osteoporatic Compression Fractures", SPINE, vol. 2, No. 14, pp. I511-1515, 2001© Lippincott Williams & Wilkins, Inc.5 pages.

Lieberman et al., "Initial Outcome and Efficacy of "Kyphoplasty" in the Treatment of Painful Osteoporatic Vertebral Compression Fractures", SPINE, vol. 26, No. 14, pp. 1631-1638, 8 pages, 2001.

* cited by examiner

DEVICES FOR INJECTING A CURABLE BIOMATERIAL INTO A INTERVERTEBRAL SPACE

REFERENCE TO RELATED APPLICATION

The present application claims priority to co-pending provisional application No. 60/583,665, entitled "SYSTEMS AND METHODS FOR INJECTING A CURABLE BIOMATERIAL INTO AN INTERVERTEBRAL SPACE", filed on Jun. 29, 2004, the entire disclosure of which is incorporated herein by reference.

BACKGROUND OF THE INVENTION

The present invention relates to systems and methods for the treatment of the spine, and especially the interbody disc space. More specifically, the invention concerns the injection of a biomaterial into a spinal space, such as the intradiscal space.

Spine fusion procedures represent the state of the art treatment for intervertebral disc problems, which generally involve open surgery and the use of interbody fusion cages and spinal fixation systems to stabilize the fusion site. An alternative treatment under evaluation is to replace the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices use a deflated balloon attached to a cannula and inserted between the vertebral bodies. The balloon is inflated with a prosthetic fluid through the cannula to distract the vertebral bodies. This requires high-pressure delivery of the fluid to achieve the pressure needed to distract the vertebral bodies and the balloon and fluid permanently remain in the disc space. Alternatively, a separate device is used to inject the prosthetic fluid around the balloon and the balloon is used strictly for distraction after which it is deflated and removed.

U.S. Pat. No. 4,772,287 ("Ray I") discloses a bladder injected with thixotropic gel implanted between two vertebral bodies to restore the disc height. The technique described requires that the vertebral bodies are first distracted and a bore drilled to allow for insertion of the bladder.

U.S. Pat. No. 5,562,736 ("Ray II") discloses a method for implanting a prosthetic disc nucleus. Ray II discloses cutting a first and second flap in the annulus. The flaps provide access to the nucleus. Ray II then discloses using an inflatable jack to distract the disc space prior to insertion of the prosthetic spinal disc nucleus. The jack has a deflated balloon on its end that is inserted into the nucleus through one of the flaps. The balloon is inflated with fluid causing the vertebral bodies to distract. Once the vertebral bodies are sufficiently distracted the fluid flow is stopped and the prosthetic spinal disc nucleus is inserted through the other flap. The balloon is then deflated and the second prosthetic spinal disc nucleus is inserted. The flaps are closed and placed in contact with the annulus by a suture, staple or glue.

U.S. Pat. No. 6,187,048 ("Milner") discloses an implant for an intervertebral disc nucleus pulposus prosthesis made from a conformable, in-situ curable, material which is resiliently deformable. Milner discloses removing the nucleus material, then either injecting through the annulus or creating an opening in the annulus to deliver a curable material under pressure into the nucleus space. The pressure is necessary to ensure conformation to the nucleus space and/or to increase the internal pressure of the disc space to distract the vertebral bodies. The amount of pressure needed to distract the disc space is high and may allow the material to flow through cracks or voids in the annulus into the disc space. Milner also describes an embodiment where the curable material is injected into a flexible container that is inserted first into the nucleus space in a deflated state and inflated by the material as the material is injected. This method relies on the pressure of the fluid as it is injected to distract the vertebral bodies. Although this avoids the problem of the material leaking through the annulus, it imposes certain constraints such as a designing a cover of the correct shape and size suitable for safe injection of the curable material and prevention of leakage of the material from the cover once filled.

U.S. Pat. No. 6,248,131 ("Felt") describes distracting and injecting at the same time using a balloon device. The balloon can be used as a shell for containing the injected curable biomaterial and also used as a distraction means as the material is injected. Another embodiment describes the balloon as a cylinder shape which when inflated inside the disc space bears against the endplates for the vertebral bodies and distracts them. Then a second device is used to inject the curable biomaterial around the balloon cylinder. The material is allowed to cure and then the balloon is removed and a second curable biomaterial can be injected into the space left where the balloon was. In sum, when Felt discloses injecting material outside of the balloon, Felt discloses using a second device to carry out the injection. Insertion of this second device into the disc should typically require a second breach of the annulus fibrosis.

Much of the prior art contemplates free injection of biomaterial into a spinal space which may lead to uncontrolled leakage. The art also describes injection of the material into a deflated balloon, which requires leaving the balloon inside the disc space. Lastly, some methods require insertion under high pressure, thereby creating a potential for the prosthetic fluid to ooze or seep out of the disc space intra-operatively.

There is therefore a need for a system and method for introducing a biomaterial into a spinal space that is not prone to the problems of the prior art, especially the leakage problem experienced by the high pressure injection systems. This need extends to systems that can be easily utilized in a minimally invasive procedure.

SUMMARY OF THE INVENTION

In order to address these needs, one embodiment of the present invention provides a vented needle assembly for use in sealably injecting biomaterial into an intradiscal space interiorly of the annulus of a spinal disc and for providing an exhaust for the intradiscal space. In accordance with one aspect, the vented needle assembly comprises a seal body having a compressible portion capable of deforming upon placement under pressure against an outer surface of the annulus of the spinal disc and a needle extending through the seal body. The needle has a distal end projecting from one surface of the seal body and has an opening thereat for passage of biomaterial therefrom into the intradiscal space. The needle also has a proximal end projecting from an opposite surface of the seal body and configured for receipt of the biomaterial. In one aspect, the needle is configured to connect to a syringe for pressure injection of the biomaterial into the needle. The vented needle assembly further comprises a vent extending through the seal body, the vent having an opening adjacent the one surface of the seal body for communication with the intradiscal space and an opening adjacent the opposite surface of the seal body for the discharge of excess biomaterial filling the intradiscal space.

In a further feature, the compressible portion of the seal body comprises a sealing face disposed at the one surface of the seal body and is capable of conforming to the outer surface of the annulus. The sealing face may be generally circular and the seal body generally cylindrical. In certain embodiments, the seal body and the sealing face are composed of an elastomeric material capable of compression under manual pressure.

In certain embodiments the vented needle assembly, the vent comprises an opening fully extending through the seal body from one surface to the other opposite surface. In other embodiments, the vent comprises a tube extending through the seal body, the tube having a distal end projecting from the one surface of the seal body and having an opening thereat for communication with the intradiscal space and having a proximal end projecting from the opposite surface of the seal body and having an opening thereat capable of communicating with air outside the spinal disc. In this embodiment, the vent tube may be formed of relatively clear material to allow visual observation of biomaterial present in the vent tube. The seal body, the needle and the vent tube may be formed as an integral unit.

The vented needle assembly may further comprise a boss portion projecting from the one surface of the body and configured for receipt into an access opening extending through the annulus of the spinal disc. The boss may be configured to have a non-circular shape, or a shape that is substantially complementary to the shape of an opening formed through the annulus. For instance, the boss may comprise a cruciate shape with the needle projecting generally through the center of the cruciate shape, the cruciate shape being defined by four generally equally spaced wings projecting radially about the needle. In one feature, the vent tube may define one of the wings.

In an alternative embodiment, the boss comprises a duckbill valve having a slit passageway extending through the boss and configured to allow expansion of the boss upon passage of biomaterial therethrough under pressure. The boss is configured in a cruciate shape formed by four wing portions, each wing portion having a respective duck-bill valve defined by a slit passageway extending therethrough.

The present invention also contemplates a kit of parts for use in the treatment of a damaged or diseased spinal disc between two opposing vertebral bodies, the disc having an inner nucleus pulposus and an outer annulus. In certain features, the kit comprises a needle assembly including a seal body and a needle extending therethrough, the seal body having a compressible portion that is adapted to be compressibly placed against the exterior surface of the annulus adjacent an opening formed through the annulus. The needle has a distal portion projecting from the seal body and is adapted to be inserted into the annulus opening in communication with the intradiscal space. The needle also has a proximal portion projecting from the seal body and adapted to receive biomaterial thereinto.

The kit further comprises an inflatable trial device adapted to be removably introduced into the intradiscal space and inflated therein with a medium capable of determining the size of the intradiscal space created by the removal of at least a portion of the nucleus pulposus. In certain embodiments, the inflatable trial device is a compliant trial balloon and the medium is a contrast medium capable of visualization under fluoroscopy.

According to certain features, the needle assembly of the kit further includes a vent tube projecting through the seal body and adapted to communicate with and exhaust the intradiscal space and to allow biomaterial to seep out when the intradiscal space is substantially filled. The kit may also include an inflatable distraction device adapted to be removably introduced into the intradiscal space and inflated therein to cause the opposed vertebral bodies to be separated further apart. The inflatable distraction device may be a non-compliant balloon adapted to provide a limit to lateral expansion but to allow further expansion in the direction of the opposing vertebral bodies.

The kit of parts may further include a quantity of curable biomaterial, the biomaterial adapted to be introduced into the needle in liquid form. The biomaterial may comprise a polymer and a crosslinker adapted to be mixed together prior to being introduced into the needle. In this case, the kit may further include a mixing device adapted to mix the polymer and the crosslinker.

It is one object to provide a system or device to facilitate introduction of a curable biomaterial into an intervertebral disc. One benefit achieved by the present invention is the ability to introduce the biomaterial under pressure and to the extent necessary to treat the affected disc. Other benefits and objects of the invention will become apparent upon consideration of the following written description, taken together with the accompanying figures.

DESCRIPTION OF THE PREFERRED EMBODIMENTS

Figure 1:
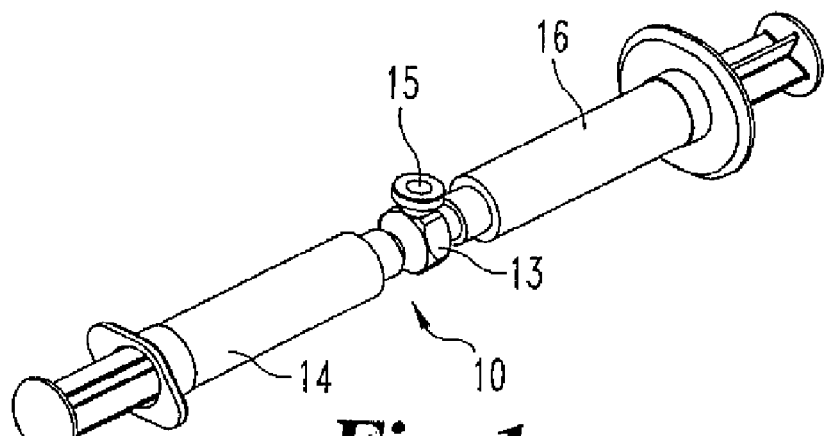
FIG. 1 is a perspective view of a mixing system for mixing an injectable biomaterial.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In one embodiment of the invention, adjacent vertebral bodies are distracted (by a non compliant balloon) at a predetermined pressure, such as at 200 psi (13 atmospheres). Using a non compliant balloon ensures that there is no lateral loading, or pressurization of the annulus, thereby avoiding the risk of damaging the annulus. The balloon (and thereby the distraction device) is then removed allowing the distracted vertebral bodies to remain distracted due to the natural stretching of the surrounding ligaments. The distraction with the balloon under pressure is held for a period of time sufficient to stretch the ligaments and to cause the distraction to be maintained even after the balloon is removed. This period of time will vary between patients; however, it in certain procedures a period of about 20-30 seconds has been sufficient. While there may be some slight contraction of the ligaments initially, the vertebral bodies will remain spaced apart at a substantially desired spacing for some time to then enable introduction of biomaterial into the distracted disc space.

The biomaterial is sealably introduced under pressure that is not as high as used for the distraction step but that is sufficient so that the biomaterial will completely fill the space (or the partial space in a partial discectomy). Moreover, the injection pressure for the biomaterial is sufficient to recover any small amount of contraction that may occur when the balloon is removed. In accordance with one feature of the invention, the injection of the biomaterial occurs under low pressure. This pressure is nominally less than 100 psi, and in specific embodiments is in the range of 25-40 psi. A vent is used to exhaust the disc space and allow body fluid and/or air as well as biomaterial to seep out when the space is filled. Seepage of biomaterial indicates a complete fill of the disc space.

The low pressure on the biomaterial is held until the biomaterial is cured. This cure time is material dependent, but often falls in the range of about 5 minutes. Maintaining the pressure until curing also maintains the distracted disc space under hydrostatic pressure. Even under the low pressure, a seal must be provided around the opening in the annulus through which biomaterial is introduced. The seal in one arrangement is disposed on the material injection tube and is applied against the exterior surface of the annulus adjacent the opening.

In one embodiment of the invention, a surgical technique is provided for the use of injectable disc nucleus (IDN) as a replacement for the natural nucleus pulposus. The IDN is preferably a curable biocompatible polymer with properties that emulate those of the natural human disc. A suitable IDN material is disclosed in U.S. Pat. Nos. 6,423,333; 6,033,654; and 5,817,033, which issued to Protein Polymer Technologies, Inc. The disclosures or these patents are incorporated herein by reference. These patents disclose a proteinaceous curable polymer that has physical properties close to those of the human disc and that includes certain adhesive properties that allow the polymer to adhere to the disc annulus and any remaining disc nucleus pulposus.

Figure 2:
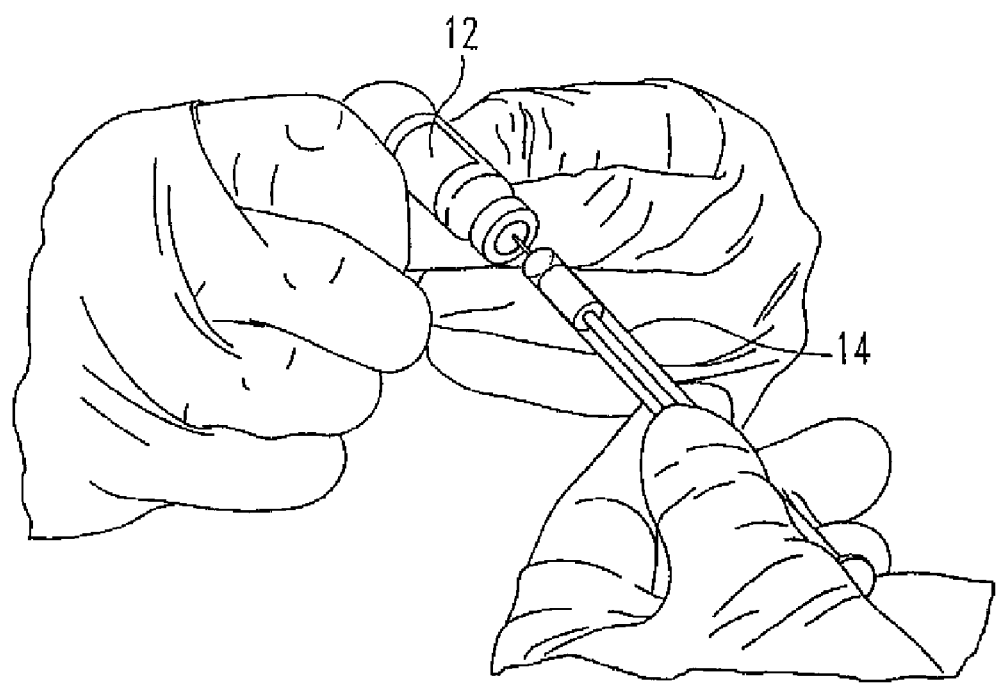
FIG. 2 is a pictorial view of the withdrawal of a cross-linker to be added to the biomaterial in the mixing system shown in FIG. 1.
Figure 3:
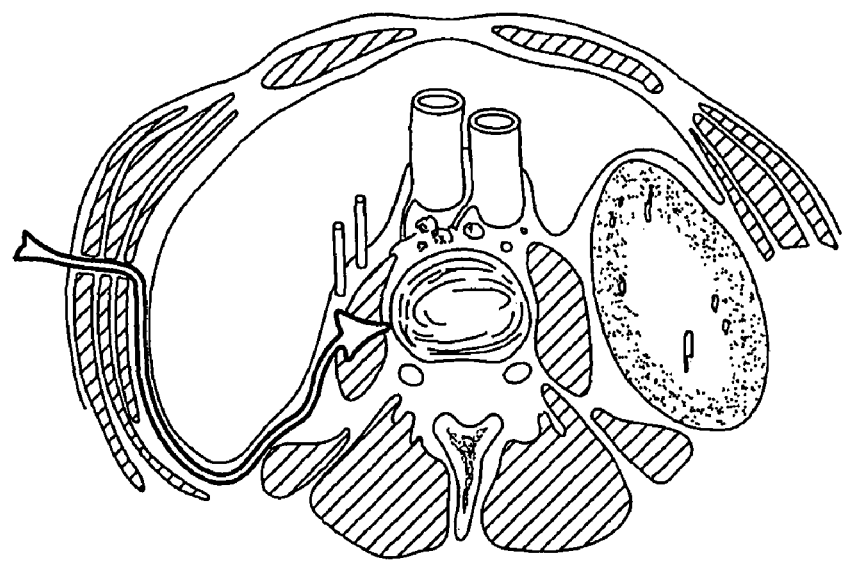
FIGS. 3-5 are diagrammatic view of surgical approaches to the intervertebral disc.
Figure 4:
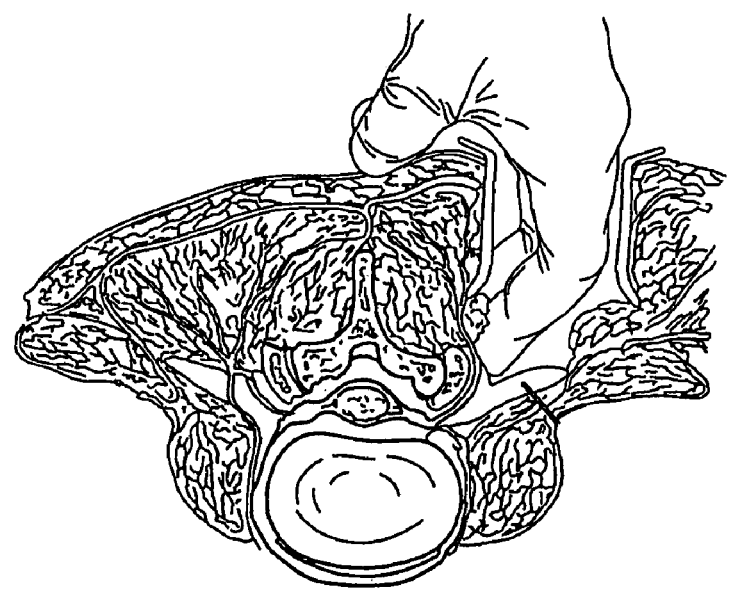
Figure 5:
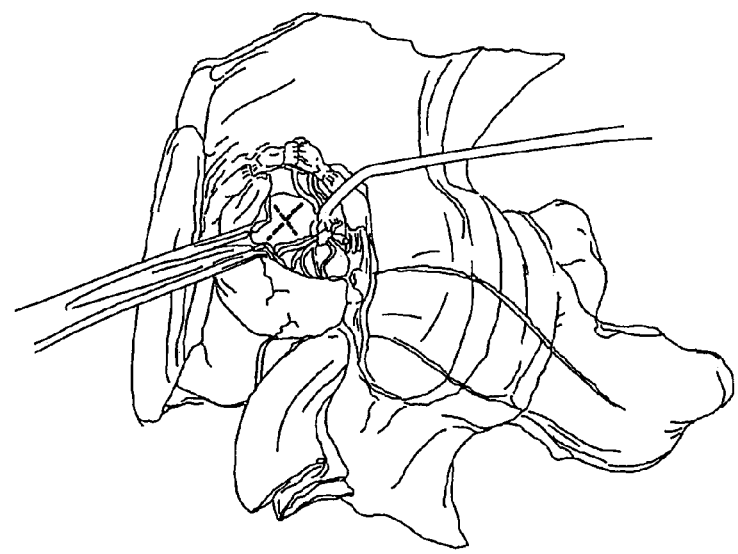

In a first step of the technique, a mixing system 10 is provided for mixing the constituents of the IDN material, as shown in FIG. 1. The mixing system 10 may be constructed as disclosed in co-pending application Ser. No. 10/803,214, entitled "Systems and Methods for Mixing Fluids". The entire disclosure of this application is incorporated herein by references, and particularly the discussion of the embodiment shown in FIGS. 3-9 in that application. In a specific embodiment, the mixing system 10 is prepared prior to the start of surgery by loading the assembly with four mL of a polymer constituent. This volume is mixed with a cross-linker constituent. In the specific embodiment, the volume is mixed with 34±1 μL of crosslinker drawn from a sterile vial 12 into a 100 μL syringe 14, purged of air, as shown in FIG. 2. The syringe is placed on the sterile table until it is needed for the mixing and injection step.

Where the biomaterial is an IDN, access to the intradiscal space is required. While many surgical approaches may be used, in one specific embodiment, the surgeon will use an extraforaminal mini-open approach to the disc. This may be either by a lateral retroperitoneal approach (FIG. 3) or a paramedian approach (FIG. 4) through the paraspinal muscles of the back. Access to the nucleus is gained through an extraforaminal annulotomy, so as to not expose the spinal canal or foramen to any undue risk. The annulus is identified and a minimal annulotomy is performed to gain access to the intradiscal space. If necessary, a cruciate annulotomy of up to 5 mm×5 mm may be used. The annulotomy should be oriented obliquely with one cut oriented with the outer fibers of the annulus, as shown in FIG. 5. The nucleus pulposus is then partially or completely removed using known techniques, such as using pituitary rongeurs and/or curettes. Alternatively, a mechanical method such as endoscopic shaving, hydraulic or radiofrequency (RF) technology may be used. The nucleotomy should be fully irrigated once all loose fragments have been manually removed.

Figure 6:
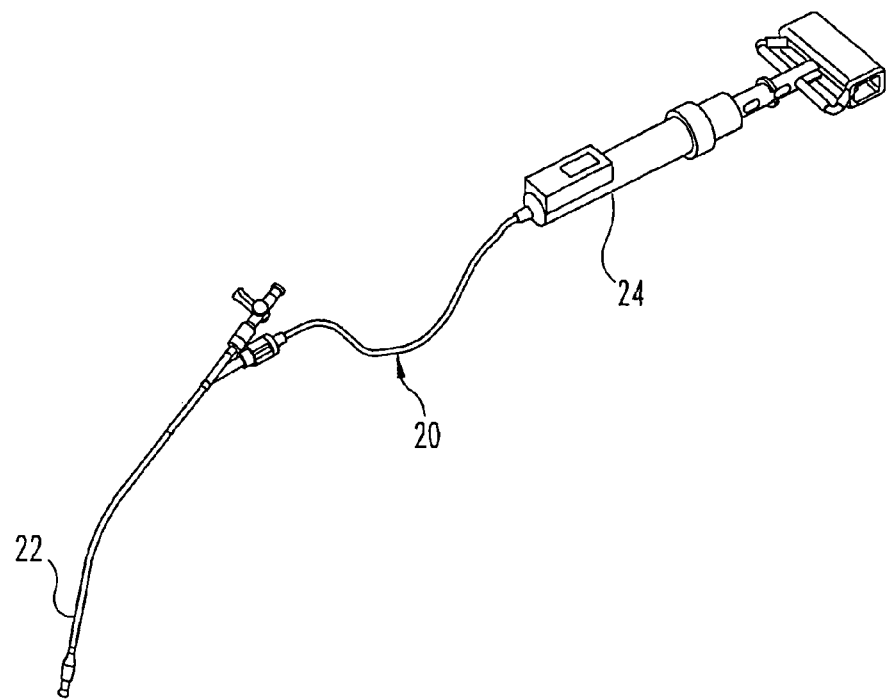
FIG. 6 is a pictorial view of a trial balloon assembly for use in a method of one embodiment of the present invention.
Figure 7:
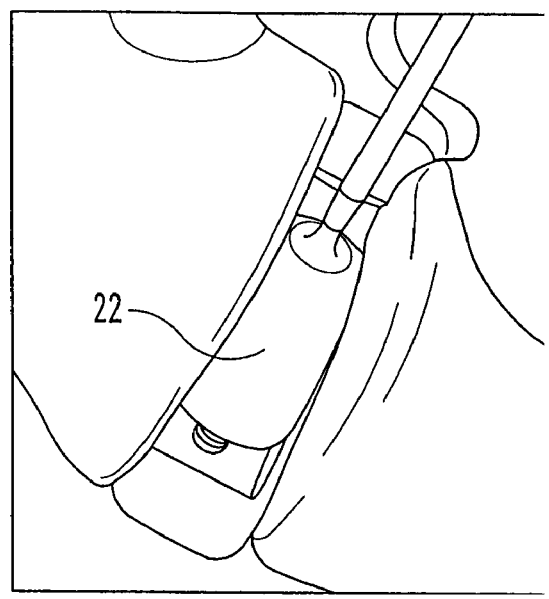
FIG. 7 is a pictorial representation of the use of the trial balloon shown in FIG. 6 in accordance with one aspect of the invention.
Figure 17:
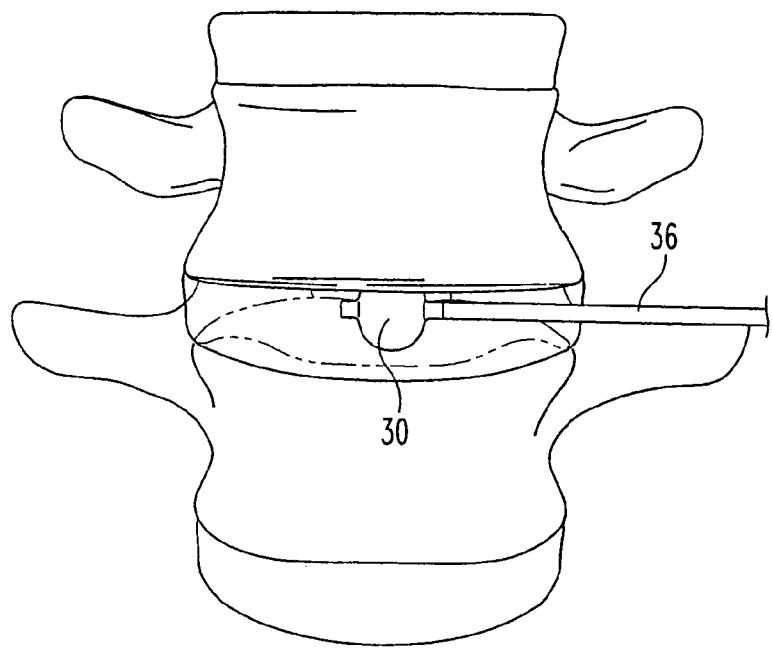
FIG. 17 is an enlarged pictorial view of the distraction balloon shown in FIG. 9.

The prepared nuclear cavity should be visualized prior to proceeding using a compliant trial balloon assembly 20, as depicted in FIG. 6. Once the balloon 22 is assembled to the inflation syringe 24 and primed with an inflation medium, the balloon is inserted through the annulotomy until it stops against the far border of the nucleotomy space. Preferably, the inflation medium is a fluid contrast medium that can be visualized under fluoroscopy. Injection of contrast media into the balloon and inflation under light pressure will allow the surgeon to judge the location and size of the space (FIGS. 7 and 17). In certain embodiments, the disc space can be visualized and the inflated size of the trial balloon measured to determine the distracted size of the disc space. An endoscopic camera may also be used to inspect the interior of the nucleotomy space, if desired by the surgeon.

If further removal of nucleus pulposus is indicated, the balloon can be removed and the nucleotomy continued. This iterative process may be repeated until the surgeon is satisfied with the size and location of the nucleotomy. In one feature of the invention, the final volume of contrast media injected into the balloon may then be used to estimate the volume of the nucleotomy and determine the amount of IDN that will be needed to fill the space.

Figure 8:
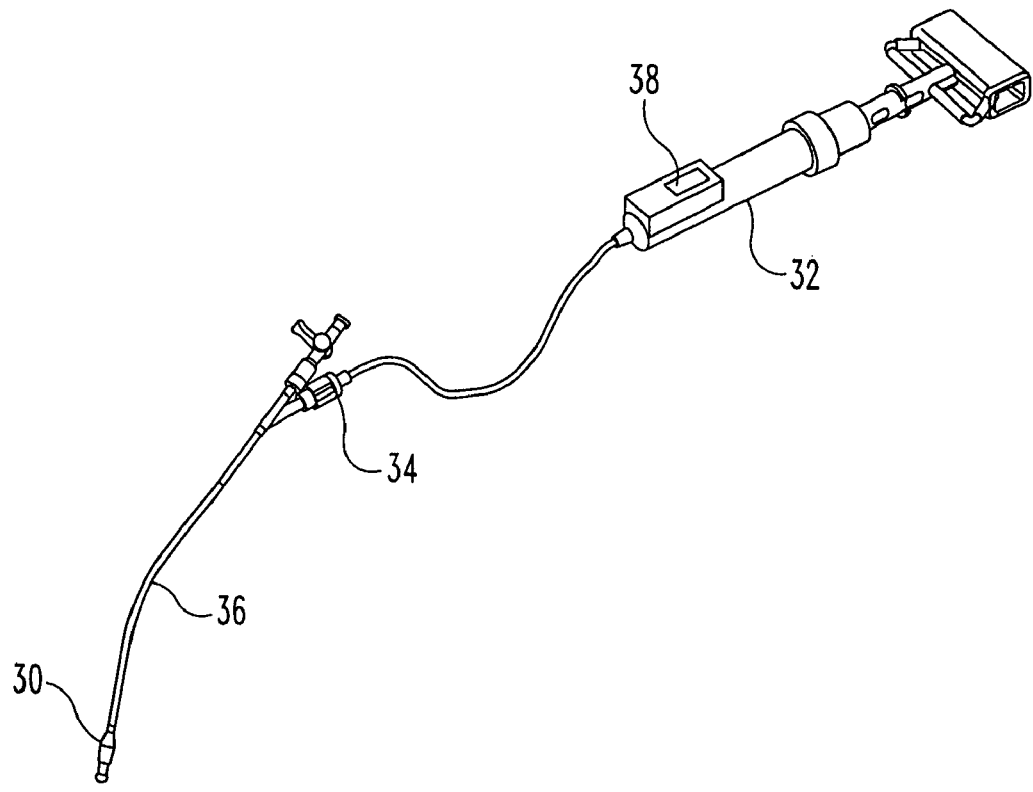
FIG. 8 is a pictorial view of a distraction balloon for use in a further aspect of the present invention.

Once the size of the space has been determined, the next step of the present invention involves distracting the space. In one embodiment, distraction of the disc is accomplished using a spherical balloon 30, such as a 15 mm diameter spherical balloon. The balloon is made of a non-compliant material and is adapted to provide a distraction force against the endplates of the disc. In a specific embodiment, the balloon 30 is able to be pressurized to approximately 13 atmospheres (200 psi). It is inflated using an inflation syringe 32 attached to the Luer fitting 34 on the catheter 36 of the balloon, as shown in FIG. 8. Pressure feedback is preferably obtained through tactile feel in the inflation syringe and a pressure gage 38 mounted on the body of the inflation syringe.

Figure 9:
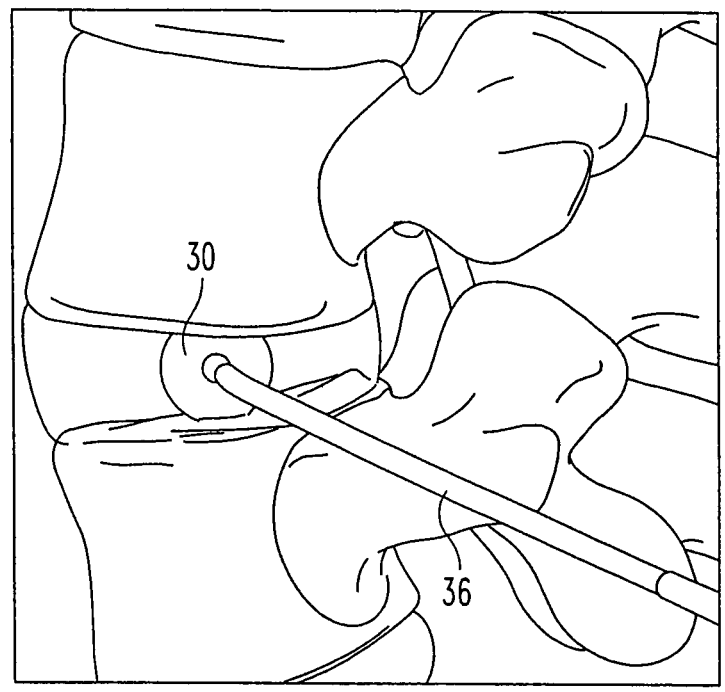
FIG. 9 is a pictorial representation of the distraction balloon of FIG. 8 shown in situ.
Figure 10:
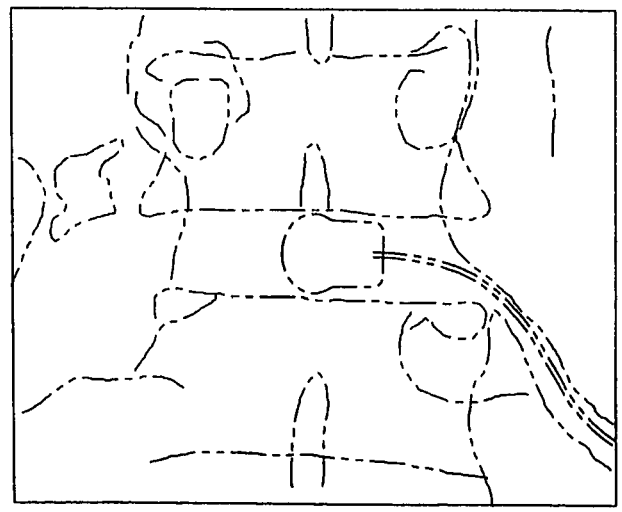
FIG. 10 is a fluoroscopic view of a distraction balloon in situ.

Once the syringe and balloon are primed with contrast media, the balloon is inserted into the disc space until it stops against the far border of the nucleotomy, as shown in FIG. 9. The balloon is gradually inflated until it contacts the endplates and ultimately pushes apart the endplates to achieve the desired amount of distraction (FIG. 10). Care should be taken to ensure the pressure rating of the balloon is not exceeded and that the endplates are not compromised by over-distraction.

Once the desired amount of distraction has been obtained, the balloon is deflated and removed from the disc. At this point, the trial balloon 22 may be used again to evaluate the resulting final nucleotomy. If the trial balloon is re-used, the resulting fluid volume may again be used to estimate the volume of IDN needed to the fill the distracted space.

Alternatively, distraction may be obtained using the surgeon's preferred technique. Other distraction techniques such as laminar distraction, screw/pin distraction, patient positioning, and traction may be used. As preservation of an intact endplate is important, the distraction technique may need to be altered from patient to patient in order to address this matter. One technique may be preferred over others in certain instances due to patient bone quality and anatomy. If additional distraction is applied, the trial balloon 22 may be used again to provide an estimate of the requisite IDN fluid volume.

In one feature of the invention, the distraction of the disc space is maintained by the patient's anatomy, rather than by a distraction device maintained in the disc space. It has been found that if the distraction accomplished as described above is maintained for a certain length of time the spinal ligaments will stretch and retain their lengthened configuration for sufficient time to inject the IDN and allow it to cure. In a specific embodiment, maintaining the distraction for about five minutes was sufficient to cause the surrounding ligaments to maintain the distraction long enough to complete the IDN injection and curing process.

Figure 11:
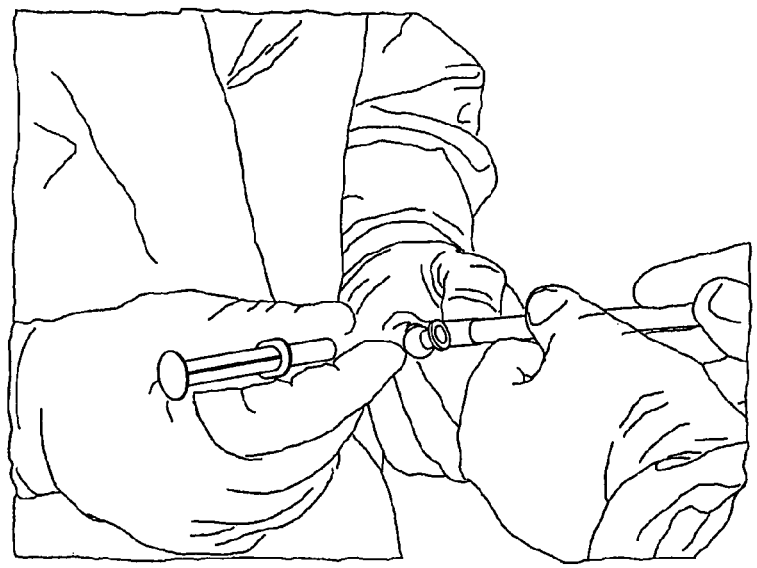
FIG. 11 is a pictorial view of the injection of the cross-linker into the biomaterial mixing system.

Immediately prior to injection, suction is applied to the cavity formed by the removal of tissue during the nucleotomy. A surgical swab may also be used to wick away excess moisture from the injection site. This will ensure that excess fluid does not interfere with the injection of the IDN material. Once the injection site has been prepared, the surgeon will hold the mixing assembly 10 with the crosslinker injection port 15 oriented upward. The entire volume of polymer should now reside in one syringe 14. The sterile assistant will inject the pre-measured volume of crosslinker from the crosslinker syringe 14 into the mixing assembly 10 through the port 15 in adaptor 13 (FIG. 1), as shown in FIG. 11.

Figure 12:
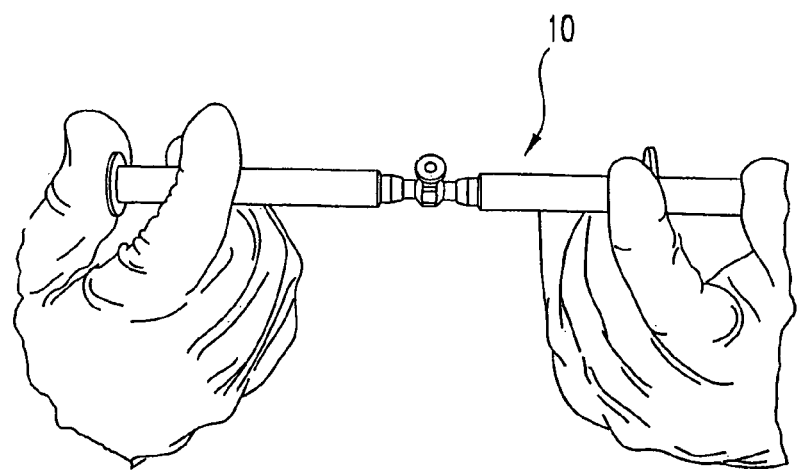
FIG. 12 is a pictorial view of the step of mixing the biomaterial within the mixing system.

The surgeon then mixes the crosslinker and polymer by cycling the plungers of the syringes 14 and 16 back and forth a predetermined number of cycles that is based upon the properties of the particular polymer. For the proteinaceous polymers disclosed in the Protein Polymer patents described above, the plungers are preferably cycled through ten full cycles in ten seconds (FIG. 12). For these polymers, it is important to complete the mixing procedure in ten seconds or less in order to ensure complete and proper mixing of the IDN. Upon completion of the mixing step, the surgeon disassembles the syringe 14 (no insert in the syringe) from the adapter 13. From this point, the surgeon has a fixed amount of working time to perform the injection using the second syringe 16. With the specific polymers, this working time is about 80 seconds. An appropriate previously selected injection needle is connected to the tip of the syringe 16 and the needle is primed with the fully mixed biomaterial composition prior to introducing the needle to the injection site. The initial drops from the injection needle can be ejected onto the surgical field and used as a qualitative gage of the working time of the IDN during the injection procedure.

Figure 13:
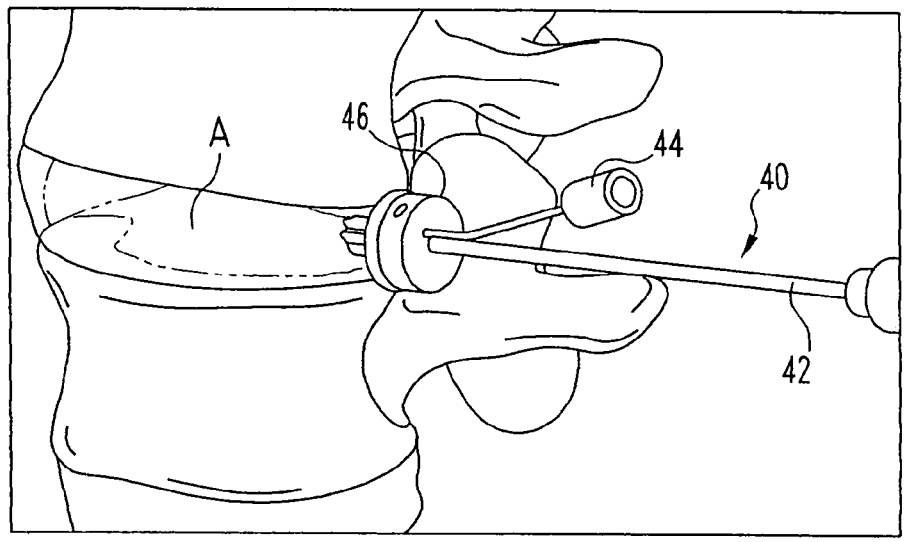
FIG. 13 is a pictorial representation of a vented injection needle assembly in accordance with one aspect of the present invention.

In accordance with one aspect of the invention, the injection needle is provided as part of an injection assembly 40, as shown in FIG. 13. The injection needle 42 extends through a seal element 46 that is configured to provide an essentially fluid tight seal against the disc annulus A. A vent 44 also extends through the seal 46. The seal 46 is shown in more detail in FIG. 15. In the preferred embodiment of the invention, the seal 46 includes a body 48 that is preferably formed of a resilient material that can be compressed slightly under manual pressure against the disc annulus around the annulotomy cut in the annulus. The body 48 defines a sealing face 50 that bears against the disc annulus A (FIG. 13) to form the fluid tight seal.

Figure 15:
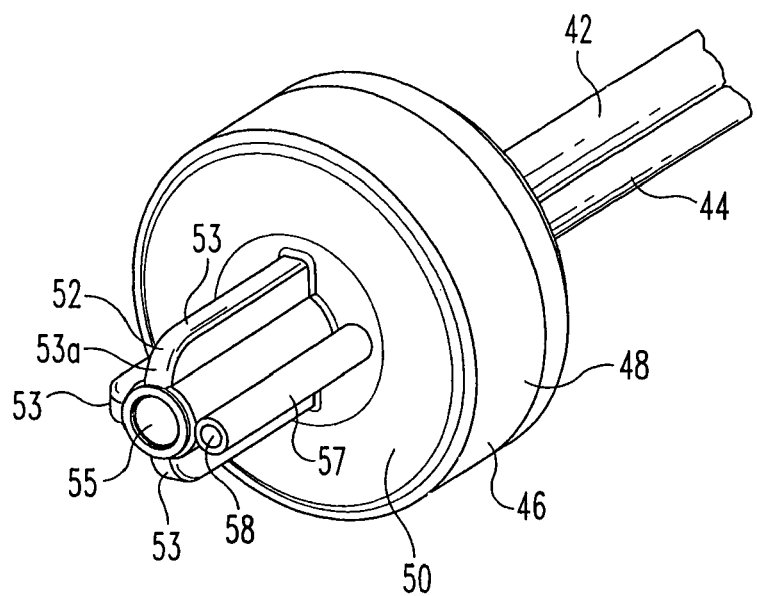
FIG. 15 is a front perspective enlarged view of the vented injection needle in accordance with one embodiment of the invention.

Extending from the sealing face 50 is an engagement boss 52. The boss 52 is preferably configured in accordance with the shape of the annulotomy cut into the annulus. In the illustrated and most preferred embodiment, the annulotomy is cruciate, so that boss 52 is also cruciate in shape. In particular, the boss 52 includes wings 53 that are sized to fit within corresponding legs of the cruciate cut into the annulus A. The leading edges 53a of the wings 53 can be rounded, as shown in FIG. 15, to facilitate placement of the boss 52 within the annulotomy.

The vent 44 provides an additional wing 57 for the boss 52. The wing 57 includes a channel 58 that integrates with the hollow vent 44. Preferably, the vent wing 57 is co-extensive with the other wings of the boss 52. Alternatively, the working end of the wing 57 can project slightly farther into the disc space. The injection needle 42 feeds to a channel 55 defined in the boss 52 to provide a pathway for the IDN into the disc cavity.

Figure 14:
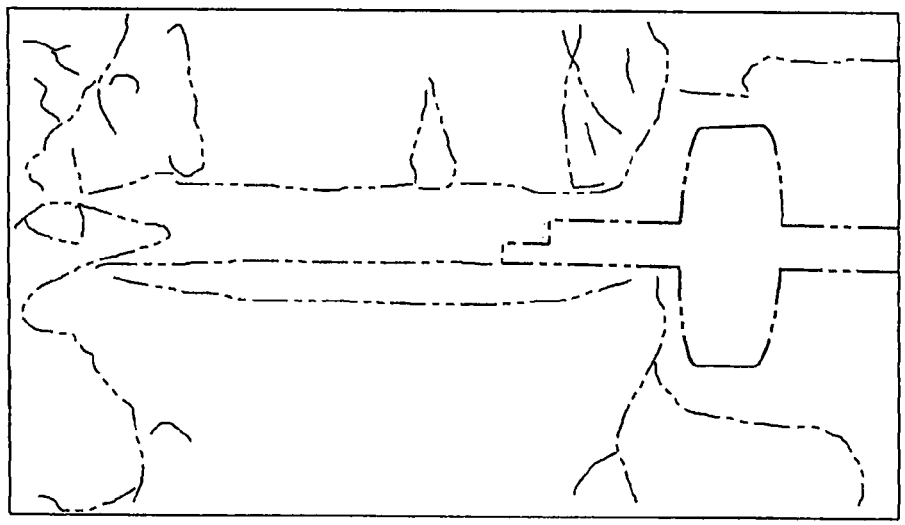
FIG. 14 is a fluoroscopic view of the vented injection needle assembly of FIG. 13 shown in situ.
Figure 16:
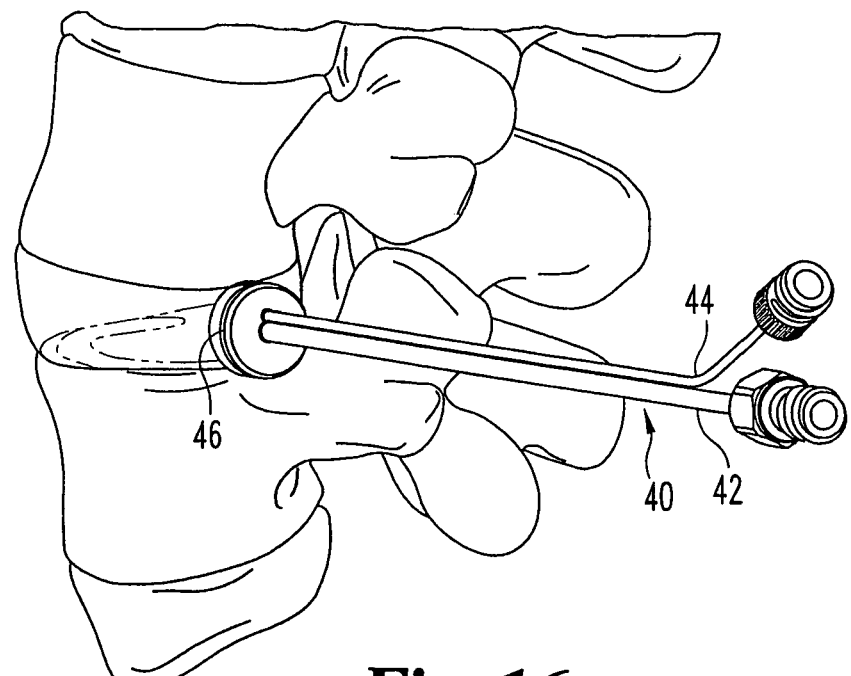
FIG. 16 is an enlarged pictorial view of the vented injection needle depicted in FIG. 15 shown in situ.

In accordance with the preferred method of the invention, the needle is introduced through the annulotomy, while carefully retracting the nerve root, until the seal 46 seats against the annulus, as depicted in FIGS. 13-14. Preferably, the needle is positioned so that the vent 44 is facing upward during the injection, as depicted in FIG. 16. Pressure is applied to the seal 46 to ensure no IDN leaks out between the seal and annulus. Preferably, this pressure is applied manually by the surgeon by simply pressing the injection needle 42 toward the annulus. Since the IDN injection occurs at low pressures, the amount of force required to maintain a fluid-tight seal between the seal face 50 and the annulus is minimal.

Alternatively, the injection assembly 40 may be modified to incorporate various of the sealing techniques described in co-pending application Ser. No. 10/282,755, filed on Oct. 29, 2002 in the name of inventors Boyd et al., and assigned to the assignee of the present invention and application. This co-pending application, entitled "Devices and Methods for the Restoration of a Spinal Disc", was published on May 1, 2003, as Pub. No. U.S. 2003/0083641A1. The disclosure of this co-pending application and publication is incorporated herein by reference for all purposes, and specifically the disclosure of the sealing and venting techniques illustrated in FIGS. 11-14 thereof.

The IDN is injected into the space until IDN is seen flowing into or out of the vent tube. In a specific embodiment, the vent tube 44 is clear so that the presence of IDN fluid within the vent can be immediately detected. At this point, the injection is stopped and the needle is held in place until the IDN takes its initial set. A microscope or loupe may be used to visualize the injection process.

In accordance with the preferred embodiment of the invention, the IDN must be allowed to substantially completely cure before the injection needle assembly 40 is removed and the surgical site is closed. The cure period depends upon the particular IDN material. For the specific proteinaceous polymer discussed above, the cure period is a minimum of about five minutes. If IDN material is left within the annulotomy or external to the disc, it is preferably removed using rongeurs after the material has taken its initial set. Suction may also be used around the periphery of the annulotomy to remove cured material.

The volume of IDN injected into the site is preferably recorded from the graduations on the syringe 16. The injection volume will be the difference between the pre- and post-injection graduation readings. The wound is closed and dressed using the surgeon's preferred technique.

As explained above, the IDN is injected under low pressure, which at a minimum means enough pressure so that the IDN will fill all the space left by the excised disc material. The pressure should be sufficient so that the intradiscal cavity can be filled in an acceptable amount of time, which is determined primarily by the cure rate for the IDN. In the illustrated embodiment, the working time for the IDN (i.e., the time from complete mixing of the constituents until the IDN has cured or hardened too much to flow) is about 80 seconds. Thus, the pressure exerted through the syringe should be sufficient to completely fill the intradiscal cavity in about on minute. Manual operation of the syringe is preferred, but it is contemplated that other forms of pressurized injection of the IDN into the disc space is contemplated.

In one important aspect of the invention, the disc space is maintained in its distracted position without the use of external distractors that would otherwise interfere with the injection of the IDN into the space. In other words, using typical physical distraction techniques, the distractor itself will necessarily occupy a certain amount of space within the disc cavity, as well as in the annulotomy. This space must be eventually filled. Moreover, the additional component creates a leak path for the IDN. The present invention avoids these problems altogether.

The seal 46 is formed of a resilient and deformable material so that it can be compressed against the annulus A to form a fluid tight seal around the annulotomy cut into the annulus. In a preferred embodiment of the invention, the seal 46 is formed of SILASTIC® or a similar elastomeric material. The seal 46 in the illustrated embodiment is cylindrical with a circular sealing face 50 configured to surround the annulotomy in the annulus; however, other configurations are contemplated provided they can adequately conform to the outer surface of the disc annulus.

In a further variation, the vent 44 can simply constitute a vent opening in the seal 46. The vent tube 44 is preferred because it carries the vented fluid away from the surgical site and can bring the discharge opening within clear view of the surgeon. As a further alternative, the seal 46 can be separate from the injection needle 42 and vent tube 44. In other words, the channels 55 and 58 can extend through the body 48 of the seal 46. Catheters for the injection needle and vent can extend into the appropriate channel, preferably with a press-fit or fluid-tight engagement.

Figure 18:
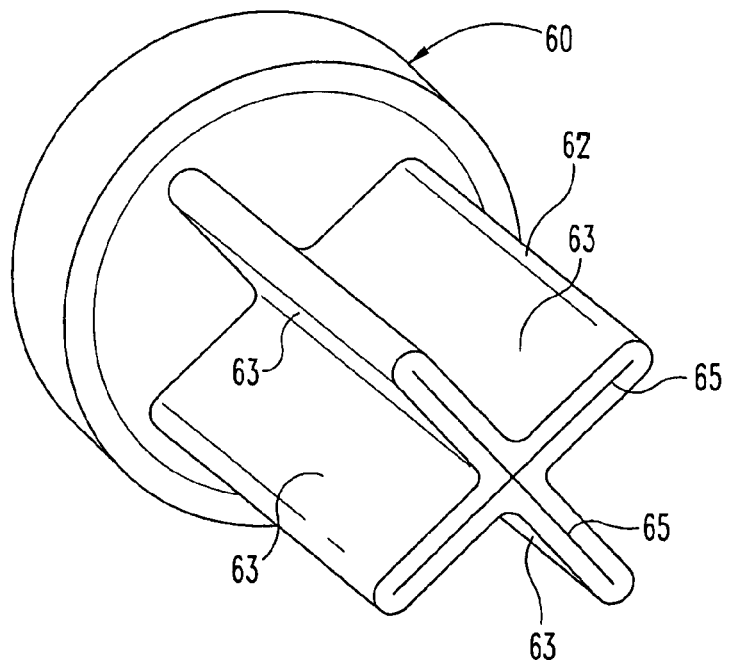
FIG. 18 is an enlarged perspective view of a seal in accordance with a further embodiment of the invention.

In yet another alternative, the cruciform boss 52 can be in the form of a duck-bill valve, as shown in FIG. 18. In particular, the seal 60 includes a valve boss 62 in the form of a cruciform duckbill valve. Each wing 63 of the boss 62 includes a slit passageway 65 that expands under fluid pressure. Thus, as fluid flows into the seal 60, the duckbill valve wings 63 expand to allow the fluid to flow into the disc space. Moreover, this expansion of the valve boss 62 enhances the seal between the cruciate boss and the annulotomy.

In the illustrated embodiment, the system and method of the present invention has been applied to the injection of an IDN into a disc space. The present system and method can be modified to provide low pressure injection of a biomaterial into other sites or cavities, such as within a vertebral body.

The present invention contemplates injection of a biomaterial into a body cavity, such as an excised disc space, under low pressure. A further feature of the invention resides in the provision of a seal against the cavity opening that can be easily maintained against the low pressure injection of the biomaterial. Another feature more specific to injection of an IDN is the method of pre-distraction of the disc space, maintaining the distraction without the use of a separate distraction tool and injecting the biomaterial into the distracted space to completely fill the space.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A vented needle assembly for use in sealably injecting a biomaterial into an intradiscal space through an access opening in the annulus of a spinal disc and for providing an exhaust for the intradiscal space, comprising:
    a compressible seal body formed of a deformable elastomeric material and having a contact surface configured to contact an outer surface of the annulus with a compressible sealing face at said contact surface of said seal body sized to surround the access opening in the annulus, said sealing face of said seal body configured to compressively deform against and in conformity with the outer surface of the annulus upon placement of said contact surface of said seal body under pressure against the outer surface of the annulus of the spinal disc;
    a needle extending through said seal body, said needle having a distal end projecting from said contact surface of said seal body and having an opening thereat for passage of the biomaterial therefrom into the intradiscal space, said needle having a proximal end projecting from an opposite surface opposite said contact surface of said seal body and configured for receipt of the biomaterial; and
    a vent tube extending through said seal body, said vent tube having a first opening extending distally beyond said contact surface of said seal body for communication with the intradiscal space and a second opening adjacent said opposite surface of said seal body for the discharge of excess biomaterial filling the intradiscal space.

2. The vented needle assembly of claim 1, wherein said sealing face is generally circular.

3. The vented needle assembly of claim 2, wherein said seal body is generally cylindrical.

4. The vented needle assembly of claim 1, wherein said vent tube has a distal end projecting from said contact surface of said seal body with said first opening thereat for communication with the intradiscal space and has a proximal end projecting from said opposite surface of said seal body with said second opening thereat capable of communicating with air outside the spinal disc.

5. The vented needle assembly of claim 4, wherein said vent tube is formed of relatively clear material to allow visual observation of biomaterial present in said vent tube.

6. The vented needle assembly of claim 4, wherein said needle is configured to connect to a syringe for pressure injection of the biomaterial into said needle.

7. The vented needle of claim 4, wherein said needle and said vent tube are joined as an integral unit.

8. The vented needle assembly of claim 4, further comprising a boss portion projecting from said contact surface of said seal body and configured for receipt into the access opening extending through the annulus of the spinal disc.

9. The vented needle assembly of claim 8, wherein said boss portion is configured to have a non-circular shape.

10. The vented needle assembly of claim 8, wherein said needle extends through said boss portion.

11. The vented needle assembly of claim 10, wherein said boss portion has a shape configured to be substantially complementary to the shape of an opening formed through the annulus.

12. A vented needle for use in sealably injecting a biomaterial into an intradiscal space through an access opening in the annulus of a spinal disc and for providing an exhaust for the intradiscal space, comprising:

a compressible seal body formed of an elastomeric material and having a contact surface configured to contact an outer surface of the annulus with a sealing face at said contact surface of said seal body sized to surround the access opening in the annulus, said seal body configured to deform against the outer surface of the annulus upon placement of said contact surface of said seal body under pressure against the outer surface of the annulus of the spinal disc, said seal body including a boss portion projecting from said contact surface and configured for receipt into the access opening extending through the annulus of the spinal disc and to be substantially complementary to the shape of an opening formed through the annulus, said boss portion having a cruciate shape;

a needle extending through said seal body with said needle projecting generally through the center of said cruciate shape, said cruciate shape being defined by four generally equally spaced wings projecting radially about said needle, said needle having a distal end having an opening thereat for passage of the biomaterial therefrom into the intradiscal space and a proximal end projecting from an opposite surface opposite said contact surface of said seal body and configured for receipt of the biomaterial; and a vent extending through said seal body, said vent having an opening adjacent said contact surface of said seal body for communication with the intradiscal space and an opening adjacent said opposite surface of said seal body for the discharge of excess biomaterial filling the intradiscal space.

13. A vented needle for use in sealably injecting a biomaterial into an intradiscal space through an access opening in the annulus of a spinal disc and for providing an exhaust for the intradiscal space, comprising:

a compressible seal body formed of an elastomeric material and having a contact surface configured to contact an outer surface of the annulus with a sealing face at said contact surface of said seal body capable of deforming against the outer surface of the annulus upon placement of said contact surface of said seal body under pressure against the outer surface of the annulus of the spinal disc, said seal body including a boss portion projecting from said contact surface of said seal body and configured for receipt into the access opening extending through the annulus of the spinal disc, said boss portion defining a channel therethrough and including at least three spaced wings projecting radially about said channel;

a needle extending through said channel, said needle having a distal end projecting from said contact surface of said seal body and having an opening thereat for passage of the biomaterial therefrom into the intradiscal space, said needle having a proximal end projecting from an opposite surface opposite said contact surface of said seal body and configured for receipt of the biomaterial; and a vent tube defining one of said wings and extending through said seal body, said vent tube having an opening at said boss portion for communication with the intradiscal space and having a proximal end defining an opening at said opposite surface of said seal body capable of communicating with air outside the spinal disc.

14. A vented needle for use in sealably injecting a biomaterial into an intradiscal space through an access opening in the annulus of a spinal disc and for providing an exhaust for the intradiscal space, comprising:

a compressible seal body formed of an elastomeric material and having a contact surface configured to contact an outer surface of the annulus with a sealing face at said contact surface of said seal body sized to surround the access opening in the annulus, said seal body configured to deform against the outer surface of the annulus upon placement of said contact surface of said seal body under pressure against the outer surface of the annulus of the spinal disc, said seal body including a boss portion projecting from said contact surface and configured for receipt into the access opening extending through the annulus of the spinal disc and to be substantially complementary to the shape of an opening formed through the annulus, said boss portion including a duck-bill valve having a slit passageway extending through said boss portion and configured to allow expansion of said boss portion upon passage of biomaterial therethrough under pressure;

a needle extending into said seal body in communication with said duck-bill valve, said needle having a distal end for passage of the biomaterial therefrom through said duck-bill valve into the intradiscal space, said needle having a proximal end projecting from an opposite surface opposite said contact surface of said seal body and configured for receipt of the biomaterial; and a vent extending through said seal body, said vent having an opening adjacent said contact surface of said seal body for communication with the intradiscal space and an opening adjacent said opposite surface of said seal body for the discharge of excess biomaterial filling the intradiscal space.

15. The vented needle of claim 14, wherein said boss portion is configured in a cruciate shape formed by four wing portions, each wing portion having a respective duck-bill valve defined by a slit passageway extending through each wing portion.

16. A vented needle assembly for use in sealably injecting a biomaterial into an intradiscal space through an access opening in the annulus of a spinal disc and for providing an exhaust for the intradiscal space, comprising as an integral unit:

a compressible seal body formed of a deformable elastomeric material and of generally cylindrical configuration having a compressible sealing face on one surface configured for sealably pressing against and for compressively deforming in conformity with the outer surface of the annulus around the access opening and an opposite surface facing away from the annulus;

a needle extending axially through said seal body, said needle having a distal end projecting from said one surface of said seal body and having an opening for communication with the intradiscal space for passage of biomaterial thereto, said needle having a proximal end projecting from said opposite surface of said seal body and configured for receipt of the biomaterial; and a vent tube extending axially through said seal body, said vent tube having a distal end projecting from said one surface of said seal body and having an opening for communication with the intradiscal space, said vent tube having a proximal end projecting from said opposite surface of said seal body and having an opening thereat capable of communicating with the air outside the spinal disc.

17. The vented needle assembly of claim 16, wherein said sealing face is generally circular.

18. The vented needle assembly of claim 16, wherein said needle is configured to connect to a syringe for pressure injection of the biomaterial into the needle.

* * * * *